(12) United States Patent
Raja et al.

(10) Patent No.: US 10,774,019 B2
(45) Date of Patent: Sep. 15, 2020

(54) PROCESS FOR CONVERSION OF ALKANES TO ALKENES

(71) Applicant: Council of Scientific & Industrial Research, New Delhi (IN)

(72) Inventors: Thirumalaiswamy Raja, Pune (IN); Ashok Kumar Venugopal, Pune (IN); Aswathy Thareparambil Venugopalan, Pune (IN); Marimuthu Prabu, Pune (IN)

(73) Assignee: COUNCIL OF SCIENTIFIC AND INDUSTRIAL RESEARCH (IN)

( * ) Notice: Subject to any disclaimer, the term of this patent is extended or adjusted under 35 U.S.C. 154(b) by 0 days.

(21) Appl. No.: 16/348,239

(22) PCT Filed: Nov. 8, 2017

(86) PCT No.: PCT/IN2017/050515
§ 371 (c)(1),
(2) Date: May 8, 2019

(87) PCT Pub. No.: WO2018/087777
PCT Pub. Date: May 17, 2018

(65) Prior Publication Data
US 2019/0315668 A1 Oct. 17, 2019

(30) Foreign Application Priority Data
Nov. 8, 2016 (IN) .............................. 201611038068

(51) Int. Cl.
*C07C 5/48* (2006.01)
*B01J 23/00* (2006.01)
(Continued)

(52) U.S. Cl.
CPC ............... *C07C 5/48* (2013.01); *B01J 23/002* (2013.01); *B01J 23/75* (2013.01); *B01J 2523/23* (2013.01); *B01J 2523/24* (2013.01); *B01J 2523/47* (2013.01); *B01J 2523/72* (2013.01); *C07C 11/04* (2013.01); *C07C 11/08* (2013.01); *C07C 2523/34* (2013.01); *C07C 2523/75* (2013.01)

(58) Field of Classification Search
None
See application file for complete search history.

(56) References Cited

U.S. PATENT DOCUMENTS 5,593,935 A 1/1997 Golunski et al.
6,730,808 B2 5/2004 Bitterlich et al.
(Continued)

FOREIGN PATENT DOCUMENTS

EP 0832056 B1 5/2001

OTHER PUBLICATIONS

Brik, Y., et al. "Titania-Supported Cobalt and Cobalt—Phosphorus Catalysts: Characterization and Performances in Ethane Oxidative Dehydrogenation," Journal of Catalysis; 2001, 202 (1), pp. 118-128.
(Continued)

*Primary Examiner* — Philip Y Louie
(74) *Attorney, Agent, or Firm* — The Belles Group, P.C.

(57) ABSTRACT

The present invention discloses an improved process for the conversion of alkanes to alkenes in the presence of a recyclable mixed oxide and perovskite catalysts with high yield.

8 Claims, 8 Drawing Sheets

(51) Int. Cl.
    B01J 23/75    (2006.01)
    C07C 11/04    (2006.01)
    C07C 11/08    (2006.01)

(56) References Cited

U.S. PATENT DOCUMENTS

| | | |
|---|---|---|
| 6,858,768 B2 | 2/2005 | Budin et al. |
| 2003/0065235 A1 | 4/2003 | Allison et al. |
| 2004/0225165 A1* | 11/2004 | Allison .................. C07C 29/06 568/910.5 |
| 2016/0074844 A1 | 3/2016 | Freer et al. |

OTHER PUBLICATIONS

Donsi, F., et al. "Oxidative dehydrogenation of ethane over a perovskite-based monolithic reactor," Journal of Catalysis, 2002, 209, pp. 51-61.

Hayakawa, T., et al. "Oxidative dehydrogenation of ethane over some titanates based perovskite oxides," Catalysis Letters, 1992, 16 (4), pp. 373-387.

Velle, OJ, et al. "The oxidative dehydrogenation of ethane by perovskite type catalysts containing oxides of strontium, cerium and ytterbium," Catalysis Today, 1990, 6 (4), pp. 567-574.

Watanabe, R., et al."Lanthanoid-free perovskite oxide catalyst for dehydrogenation of ethylbenzene working with redox mechanism," Front Chem.; 2013; 1; 21.

Watanabe, R., et al. "Novel Perovskite-Type Oxide Catalysts for Dehydrogenation of Ethylbenzene to Styrene," Catalysis Letters, 2009, 131 (1-2), pp. 54-58.

International Search Report and Written Opinion, PCT/IN2017/050515, dated Feb. 21, 2018, pp. 1-8.

\* cited by examiner

PROCESS FOR CONVERSION OF ALKANES TO ALKENES

CROSS-REFERENCE TO RELATED APPLICATIONS

This application is a National Stage of International Application No. PCT/IN2017/050515, filed Nov. 8, 2017, which claims the benefit of Indian Application No. 201611038068, filed on Nov. 8, 2016. The disclosures of the above applications are incorporated herein by reference.

FIELD OF THE INVENTION

The present invention relates to a process for the conversion of alkanes to alkenes. More particularly, the present invention relates to an improved process for the conversion of alkanes to alkenes in the presence of a recyclable mixed oxide and perovskite catalysts with high yield.

BACKGROUND AND PRIOR ART

The selective conversion of short chain alkanes namely ethane, propane and butane (a by-product of petroleum processing and present in natural/shale gas) to olefins ethylene, propylene, the butenes, and butadiene respectively are important processes owing to its high commercial value of end products. The entire capacity of $C_2$-$C_4$ olefins worldwide is produced by three commercial processes; they are i) thermal cracking (pyrolysis or steam cracking), ii) catalytic cracking and iii) catalytic dehydrogenation. These processes suffer many disadvantages like rapid deactivation, high endothermicity and thermodynamic limitations. Oxidative dehydrogenation (ODH) of light alkanes is a commercially attractive route to produce alkenes. The main advantage is the exothermic nature of the reaction which avoids the thermodynamic constraints of other non-oxidative routes by forming water as a byproduct. Compared with the conventional steam-cracking method of dehydrogenating alkanes to olefins and current catalytic dehydrogenation processes, ODH could reduce costs, lower greenhouse gas emissions, and save energy. ODH can be carried out with various oxidants like oxygen, air, carbon dioxide, etc.

The products obtained by dehydrogenation of ethane and butane are commercially more important. Ethene is one of the important building block chemical which ranks first in production among organic chemicals. Ethylene is a base material for the production for variety of chemicals like low, linear low and high dense polyethylenes (LDPE, LLDPE, HDPE respectively, Ethylene dichloride (EDC), Vinyl compounds like Vinyl chloride, poly vinyl chloride (PVC), Vinyl acetate (VAM), Styrene and many functionalized compounds. This starts well with butane dehydrogenation where the product distribution is wide when compared to propane and ethane. On the other hand the major products formed during butane dehydrogenation is 1-butene, 2-butene (including cis and trans), 1,3-butadiene, propylene, ethylene. Components of the C4 stream are mainly consumed in the production of synthetic rubber (butadiene), polyethylene co-monomer (1-butene), specialty chemicals, engineering plastics and solvents. The main products obtained from the C4-olefins are hexa methylene diamine, Acrylonitrile, butadiene, styrene, Polymers based on butadiene and butane.

In recent years, butenes, especially 1,3-butadiene became a versatile chemical as a monomer in polymer industry. Current industrial process for the production of butenes is the steam cracking of naphtha. As an alternative method, dehydrogenation of n-butane requires high temperature and it will favor more of cracked products and increases coke formation which will lead to quick catalyst deactivation. Meanwhile researchers have put on efforts in finding a robust catalyst for an energy efficient process like oxidative dehydrogenation (ODH). A large number of metal oxide systems are studied for ODH of n-butane. Few reports for ODH of ethane, propane, octane and ethyl benzene are available over titania supported systems. Cobalt based catalysts are well known for Fischer Tropsch reaction and other related synthesis.

US20030065235A1 discloses a method for converting alkanes to olefins comprising: heating a feed stream comprising an alkane and an oxidant to a temperature of approximately 300-700° C.; contacting said feed stream with a catalyst comprising a base metal, metal oxide, or a combination thereof and a refractory support; maintaining a contact time of said alkane with said catalyst for less than 200 milliseconds; and maintaining oxidative dehydrogenation favorable conditions; wherein ethylene yield is at least 40%.

U.S. Pat. No. 6,858,768B2 discloses a method for the production of olefins by oxidative dehydrogenation wherein the method comprises the steps of: (a) forming a feed stream comprising an alkane and an oxidant; (b) heating the feed steam to a temperature of approximately 300-700° C.; (c) contacting the feed stream with a catalyst consisting essentially of one or more oxides selected from the group containing alumina, zirconia, titania, yttria, silica, niobia, and vanadia; (d) maintaining a contact time of the feed stream with said catalyst for less than 200 milliseconds under oxidative dehydrogenation favorable conditions so as to produce olefins; and (e) recovering olefins; wherein the recovered olefins include ethylene and the ethylene yield is at least 50%.

EP0832056B1 discloses a process for converting an alkane of the formula, $C_nH_{2n+2}$, to an alkene of the formula, $C_nH_{2n}$, where n is the same for the alkane and the alkene and n is from 2 to 5, the process comprising contacting the alkane in the absence of oxygen with a dehydrogenation catalyst and a solid oxygen source comprising a reducible metal oxide under conditions sufficient to selectively convert the alkane and reducible metal oxide to a reduced form of the metal oxide, the alkene, and water, wherein the dehydrogenation catalyst comprises at least one metal selected from Cr, Mo, Ga, Zn, and a Group VIII metal, and wherein the reducible metal oxide is an oxide of at least one metal selected from Bi, In, Sb, Zn, Tl, Pb and Te.

WO2006063230A1 discloses a method of converting paraffinic hydrocarbons to alkenes, comprising the steps of: employing a perovskite composition, the composition having the general formula of $BaSmTiO_3$, wherein in the composition, barium comprises from about 1 mole to about 2 moles, samarium comprises from about 0.1 mole to about 1.0 moles, and titanium comprises about 1 mole; heating a reactor which contains the composition to a temperature ranging from about 400° C. to about 500° C. using a gas and a means for heating; supplying a feed gas to the heated reactor, the feed gas comprising one or more paraffinic hydrocarbons, a quantity of oxygen, and a quantity of nitrogen, and wherein heat derived from converting the feed gas paraffinic hydrocarbon to alkenes heats the reactor to a temperature ranging from about 650° C. to about 1000° C., under conditions sufficient to convert the paraffinic hydrocarbon into one or more alkenes; and collecting the gasses exiting the reactor, wherein the alkenes are present in the collected gasses, the yield of $C_{2+}$ compounds is greater than 20%.

U.S. Pat. No. 5,593,935 discloses a dehydrogenation of an alkane to an alkene, especially isobutane to isobutene carried out in admixture with oxygen and in the absence of added steam over a dehydrogenation and oxidation catalyst comprising a platinum group metal deposited upon a support, wherein the yield of desired alkene is in the range of 15 to 40%.

Article titled "Oxidative dehydrogenation of ethane over a perovskite-based monolithic reactor" by F Donsi e al. published in *Journal of Catalysis*, 2002, 209, pp 51-61 reports oxidative dehydrogenation (ODH) of ethane investigated in a short-contact-time reactor consisting of a $LaMnO_3$-based monolithic catalyst with a honeycomb morphology. Using an ethane/air mixture with a $C_2H_6/O_2$ ratio=1.5 and a preheat temperature ranging from 250 to 400° C. results in a 55% ethylene yield.

Article titled "Oxidative dehydrogenation of ethane over some titanates based perovskite oxides" by T Hayakawa et al. published in *Catalysis Letters*, 1992, 16 (4), pp 373-387 reports a series of perovskite catalysts tested for the oxidative dehydrogenation of ethane. The composition of these catalysts covered $CaTi_{1-x}Fe_xL_{3-\delta}$, with $0 \leq x \leq 0.4$, $SrTi_{1-x}Fe_xO_{3-\delta}$, with $0 \leq x \leq 1.0$, as well as mixtures of these. The maximum yield for ethene of 52% occurred at 1023 K with x=0.8.

Article titled "The oxidative dehydrogenation of ethane by perovskite type catalysts containing oxides of strontium, cerium and ytterbium" by OJ Velle et al. published in *Catalysis Today*, 1990, 6 (4), pp 567-574 reports the compounds with the general formula $SrCe_{1-x}Yb_xO_{3-0.5x}$ characterized by X-ray diffraction (XRD), scanning electron microscope (SEM), temperature programmed reduction (TPR) and BET, and its catalytic activity with respect to dehydrogenation of ethane to ethene. The different catalyst compositions were tested in a continuous flow tubular reactor with two different partial pressures of oxygen at 500, 600 and 700° C. A maximum yield of 49% was obtained at 700° C.

Article titled "Lanthanoid-free perovskite oxide catalyst for dehydrogenation of ethylbenzene working with redox mechanism" by R Watanabe et al. published in *Front Chem.*; 2013; 1; 21 reports lanthanoid-free perovskite oxide catalyst for dehydrogenation of ethylbenzene. The $Ba_{0.4}Sr_{0.6}Fe_{0.6}Mn_{0.4}O_{3-\delta}$ showed high styrene yield of 29.2% and selectivity to styrene of 96.6% at 813 K.

Article titled "Novel Perovskite-Type Oxide Catalysts for Dehydrogenation of Ethylbenzene to Styrene" by R Watanabe published in *Catalysis Letters*, 2009, 131 (1-2), pp 54-58 reports novel $LaMnO_x$ perovskite-oxide ($ABO_3$) catalysts for effective catalytic dehydrogenation of ethylbenzene to produce styrene. Results show that the A-site in perovskite-type oxides affected catalytic dehydrogenation activities and that the B-site affected stability of the activities. The yield of styrene is in the range of 15 to 45%.

Article titled "Titania-Supported Cobalt and Cobalt-Phosphorus Catalysts: Characterization and Performances in Ethane Oxidative Dehydrogenation" by Y Brik et al. published in *Journal of Catalysis*; 2001, 202 (1), pp 118-128 reports $TiO_2$-supported Cobalt and cobalt-phosphorus catalysts prepared by impregnation and their performances in ethane oxidative dehydrogenation. The best performance in ethane ODH is achieved at 550° C. with the sample containing 7.6 wt % Co. The reaction begins with a conversion of 33% and selectivity around 75%, then it decreases to reach after 150 min on stream a stationary state at 22% of conversion and 60% selectivity.

The present invention provides an improved process for conversion of alkanes to alkenes which is economic, efficient and has high yields.

OBJECTIVE OF THE INVENTION

The main objective of the present invention is to provide an improved process for the conversion of alkanes to alkenes in the presence of a recyclable mixed oxide and perovskite catalysts with high yield.

Another object of the present invention is to provide a process for the conversion of alkanes to alkenes which is energy efficient.

One another object of the present invention is to provide a process for the conversion of alkanes to alkenes which reduces cost and has high yield.

Yet one another object of the present invention is to provide a process for the conversion of alkanes to alkenes which is environmentally friendly and emits greenhouses gases in lesser amount.

SUMMARY OF THE INVENTION

The present invention provides an improved process for the conversion of alkanes to alkenes, wherein the process comprises contacting a feed stream comprising the alkane and an oxidant with a catalyst at a temperature of 350 to 700° C. to produce corresponding alkene; wherein said catalyst is selected from Co oxide on titania or $ABO_3$ type perovskite $Sr_xCa_yTi_aMn_bO_3$ with "x" and "y" ranging from 0.1 to 0.9, "a" from 0.75 to 0.925 and "b" from 0.075 to 0.25.

In one preferred embodiment, said alkane is selected from ethane and butane.

In another preferred embodiment, said oxidant is selected from molecular oxygen ($O_2$) or Carbon dioxide ($CO_2$).

In yet another preferred embodiment, the ratio of alkane to oxidant is in the range of 1:1 to 1:5.

In still another preferred embodiment, said catalyst is selected from group consisting of $Sr_{0.3}Ca_{0.7}Ti_{0.9}Mn_{0.1}O_3$, $Sr_{0.4}Ca_{0.6}Ti_{0.9}Mn_{0.1}O_3$, $Sr_{0.5}Ca_{0.5}Ti_{0.9}Mn_{0.1}O_3$, $Sr_{0.6}Ca_{0.4}Ti_{0.9}Mn_{0.1}O_3$, $Sr_{0.7}Ca_{0.3}Ti_{0.9}Mn_{0.1}O_3$, $Sr_{0.5}Ca_{0.5}Ti_{0.925}Mn_{0.75}O_3$ and $Sr_{0.5}Ca_{0.5}Ti_{0.75}Mn_{0.25}O_3$.

In yet still another embodiment, said reaction is carried out in fixed bed reactors, fluidized bed reactors and continuous flow reactors.

In yet still another preferred embodiment, said reaction is preferably carried out in a fixed bed continuous flow reactor.

In yet still another preferred embodiment, said reaction is preferably carried out at atmospheric pressure.

In yet still another preferred embodiment, the yield of said alkene is in the range of 8 to 35 mol %.

Other objects and advantages of the present invention will be more apparent from the following description, which is not intended to limit the scope of the present disclosure.

Reaction conditions: Total reactant flow ($C_2H_6$ & $O_2$)—GHSV 6000 $h^{-1}$, atm. pressure, 1 cc Catalyst.

Figure 5:
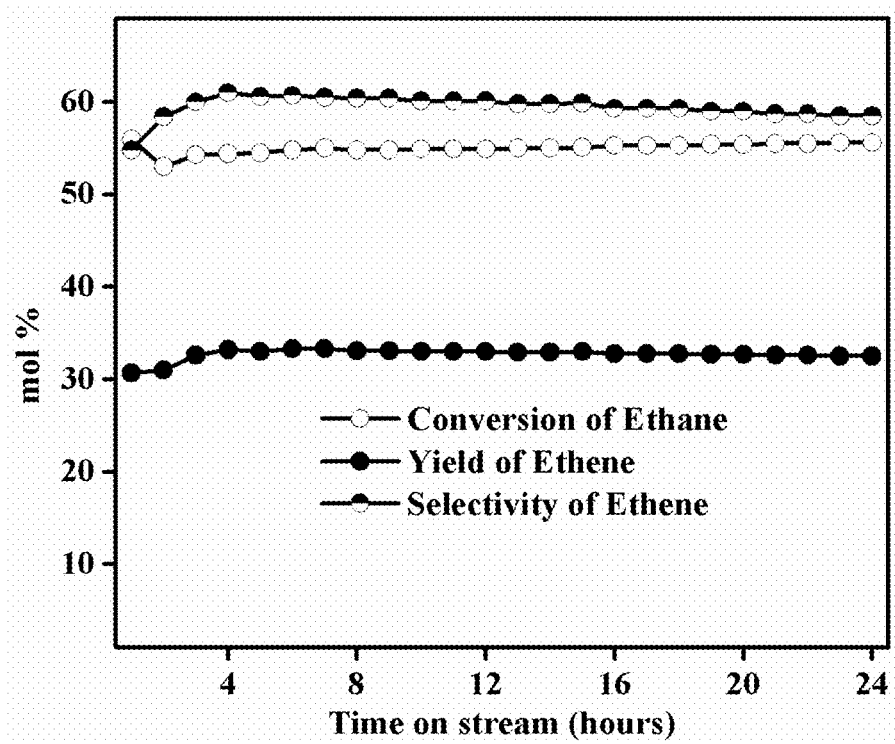

FIG. 5: depicts Time on stream study over SC5TM catalyst;
Reaction conditions: Total reactant flow ($C_2H_6$ & $O_2$)—GHSV 6000 $h^{-1}$, atm. pressure, 650° C., 1 cc catalyst.

Figure 6:
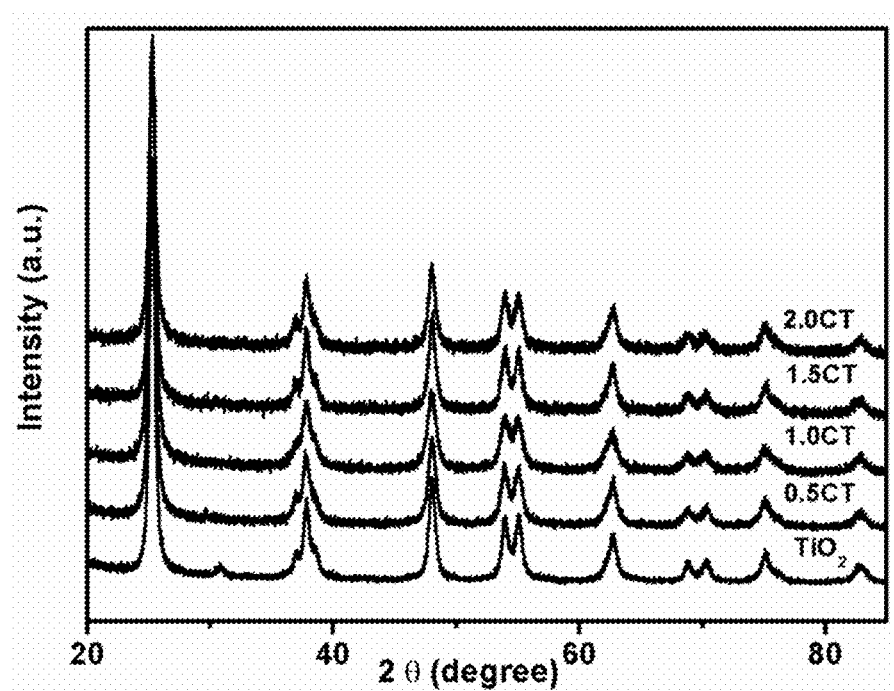

FIG. 6: depicts X-Ray diffraction patterns of synthesized catalysts.

Figure 7:
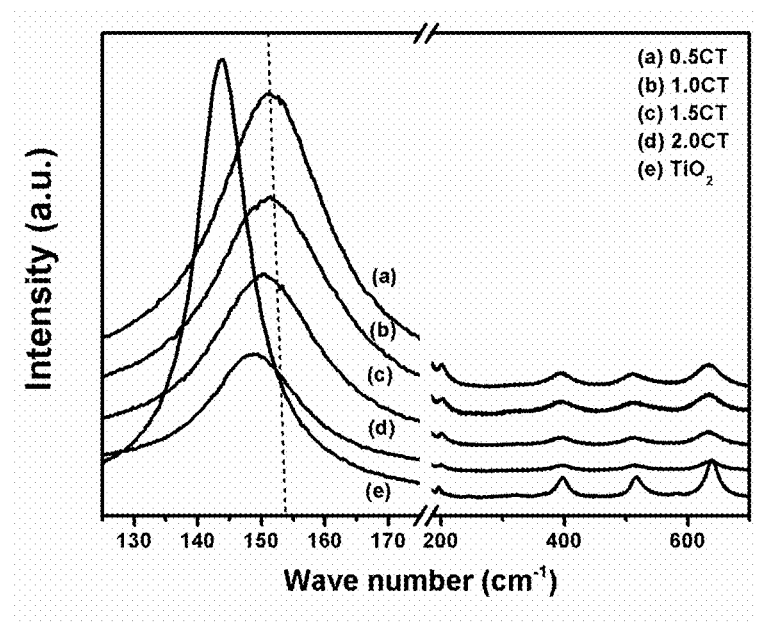

FIG. 7: depicts Raman spectra of as synthesized catalysts.

Figure 8:
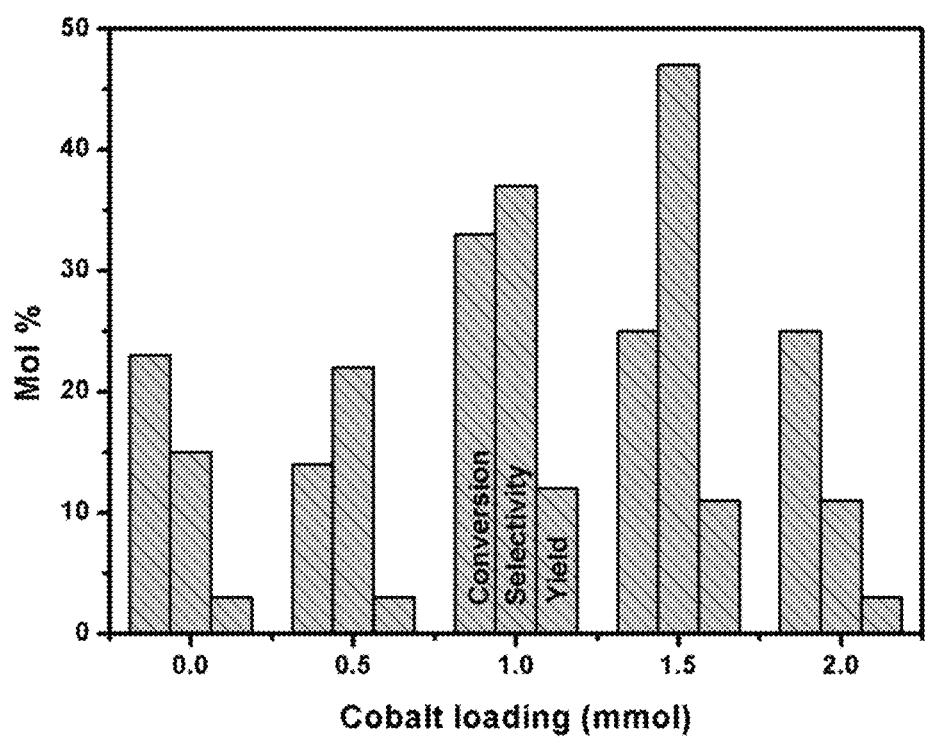

FIG. 8: depicts Catalytic activity results for ODHB over different cobalt incorporated catalysts at 400° C. with 10:10 butane to oxygen flow.

DETAILED DESCRIPTION OF THE INVENTION

The invention will now be described in detail in connection with certain preferred and optional embodiments, so that various aspects thereof may be more fully understood and appreciated.

In line with above objectives, the present invention provides an improved process for the conversion of alkanes to alkenes in the presence of recyclable mixed oxide and perovskite catalysts with high yield.

Abbreviations

ODH: Oxidative Hydrogenation;
ODHE: Oxidative Hydrogenation of ethane;
ODHB: Oxidative Hydrogenation of butane;
CT: $CaTiO_3$;
CTM: $CaTi_{0.9}Mn_{0.1}O_3$;
SC7TM: $Sr_{0.3}Ca_{0.7}Ti_{0.9}Mn_{0.1}O_3$;
SC6TM: $Sr_{0.4}Ca_{0.6}Ti_{0.9}Mn_{0.1}O_3$;
SC5TM: $Sr_{0.5}Ca_{0.5}Ti_{0.9}Mn_{0.1}O_3$;
SC4TM: $Sr_{0.6}Ca_{0.4}Ti_{0.9}Mn_{0.1}O_3$;
SC3TM: $Sr_{0.7}Ca_{0.3}Ti_{0.9}Mn_{0.1}O_3$;
SC5TM-075: $Sr_{0.5}Ca_{0.5}Ti_{0.925}Mn_{0.075}O_3$;
SC5TM-25: $Sr_{0.5}Ca_{0.5}Ti_{0.75}Mn_{0.25}O_3$;
STM: $SrTi_{0.9}Mn_{0.1}O_3$;
ST: $SrTiO_3$;
CM: $CaMnO_3$;
SEM: Scanning Electron Microscopy;
TEM: Transmission Electron Microscopy;
PXRD: Powder X-ray diffraction;
GHSV: Gas Hourly Space Velocity.

In an embodiment, the present invention provides an improved process for the conversion of alkanes to alkenes, wherein the process comprises contacting a feed stream comprising the alkane and an oxidant with a catalyst at a temperature of 350 to 700° C. to produce corresponding alkene; wherein said catalyst is selected from Co oxide on titania or $ABO_3$ type perovskite $Sr_xCa_yTi_aMn_bO_3$ with "x" and "y" ranging from 0.1 to 0.9, "a" from 0.75 to 0.925 and "b" from 0.075 to 0.25.

In one preferred embodiment, said alkane is selected from ethane and butane.

In another preferred embodiment, said oxidant is selected from molecular oxygen ($O_2$) or Carbon dioxide ($CO_2$).

In yet another preferred embodiment, the ratio of alkane to oxidant is in the range of 1:1 to 1:5.

In still another preferred embodiment, said catalyst is selected from group consisting of $Sr_{0.3}Ca_{0.7}Ti_{0.9}Mn_{0.1}O_3$, $Sr_{0.4}Ca_{0.6}Ti_{0.9}Mn_{0.1}O_3$, $Sr_{0.5}Ca_{0.5}Ti_{0.9}Mn_{0.1}O_3$, $Sr_{0.6}Ca_{0.4}Ti_{0.9}Mn_{0.1}O_3$, $Sr_{0.7}Ca_{0.3}Ti_{0.9}Mn_{0.1}O_3$, $Sr_{0.5}Ca_{0.5}Ti_{0.925}Mn_{0.75}O_3$ and $Sr_{0.5}Ca_{0.5}Ti_{0.75}Mn_{0.25}O_3$.

In yet still another preferred embodiment, said reaction is carried out in fixed bed reactors, fluidized bed reactors or continuous flow reactors.

In yet still another preferred embodiment, said reaction is preferably carried out in a fixed bed continuous flow reactor.

In yet still another preferred embodiment, said reaction is preferably carried out atmospheric pressure.

In yet still another preferred embodiment, the yield of said alkene is in the range of 8 to 35 mol %.

The process for oxidative dehydrogenation of ethane and butane with all possible products is shown below in Scheme 1:

Scheme 1

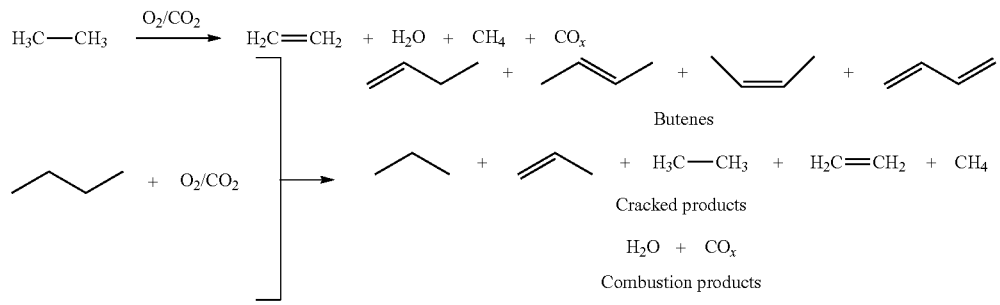

Figure 1:
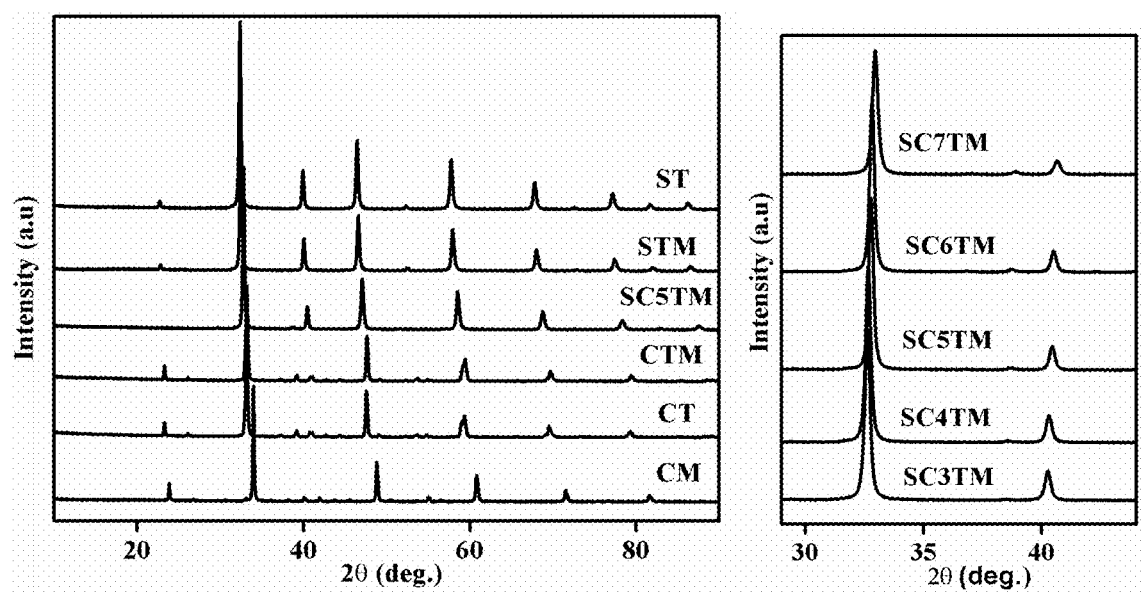
FIG. 1: depicts the Powder X-Ray diffraction patterns obtained for the all the catalysts prepared.

FIG. 1 shows the Powder X-Ray diffraction patterns obtained for the all the catalysts prepared. The end group entries $CaTiO_3$, $CaMnO_3$ and $SrTiO_3$ is indexed as orthorhombic (CT and CM) and Cubic (ST) unit cells. These patterns matched well with the JCPDS data with no. 86-1393 (CT), 86-0179 (ST) and 76-1132 (CM). The manganese substituted CT and ST showed similar patterns as that of respective parent material with slight shift in peaks to higher angle which is due to the smaller size of manganese. The other catalysts with both calcium and strontium showed a mixed phase (cubic and orthorhombic). The peak intensity of the peak at 2θ-39° corresponding to reflection of 211 plane and characteristic of orthorhombic unit cell (CT) increases as the calcium loading increases.

Figure 2:
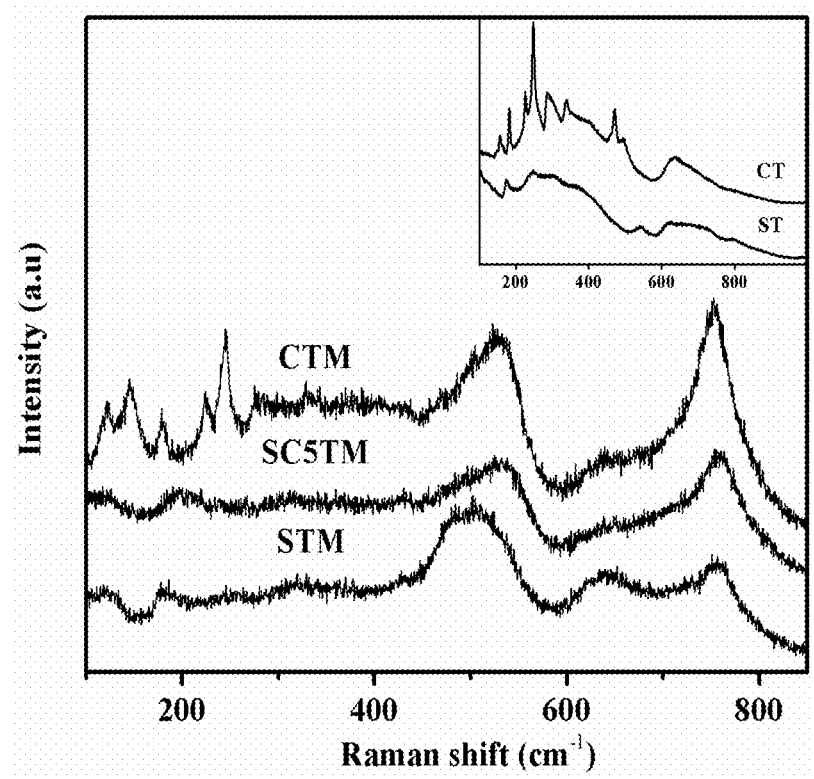
FIG. 2: depicts the Raman Spectra obtained for all the catalysts studied.

FIG. 2 shows the Raman Spectra obtained for all the catalysts studied. For CT 9 Raman modes were observed at 155, 180, 226, 247, 286, 337, 471, 495, and 639 $cm^{-1}$. The peak at 155 $cm^{-1}$ corresponds to the Ca—$TiO_3$ lattice mode and the peak at 471 $cm^{-1}$ is attributed to the Ti—$O_3$ torsional mode. For ST two broad bands centered at 300 and 700 $cm^{-1}$ were observed. In case of CTM and STM they possess similar features as their respective end group with peaks having decreased intensity. In case of SC5TM the peaks did not resemble any of the end group catalysts and the peak at 471 cm$^{-1}$ is shifted to a higher frequency at 532 cm$^{-1}$.

Figure 3:
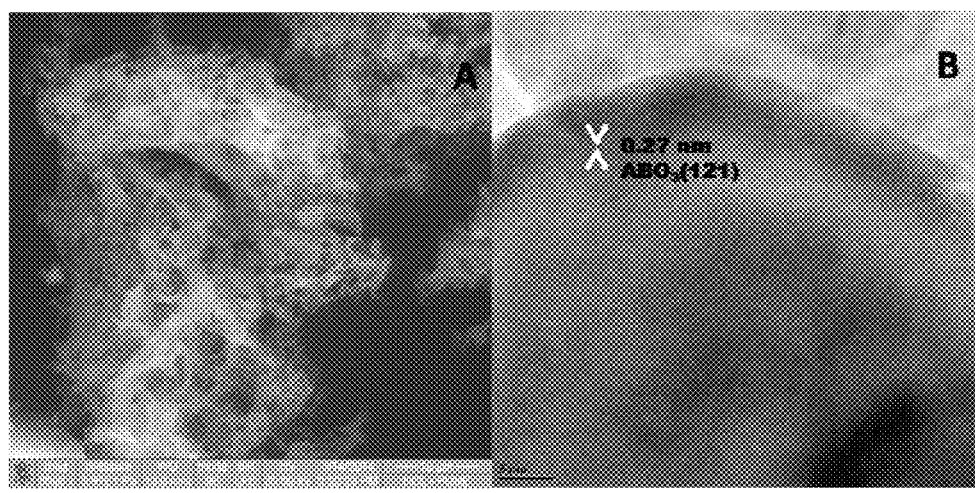
FIG. 3: depicts A) SEM of SC5TM, and B) TEM of SC5TM.

The external morphologies of the SCMT catalyst is examined by Scanning electron microscopy (SEM) technique and the representative images are shown in FIG. 3A which reveals the macroporus morphology of the catalyst. In a magnified view the sample showed fibrous morphology with large voids. Transmission Electron Microscopy (TEM) also showed similar morphology (FIG. 3B) as SEM. In higher resolution lattice a fringe corresponding to d-spacing 0.27 nm is observed which corresponds to the perovskite (121) plane, which is also in good agreement with PXRD.

Figure 4:
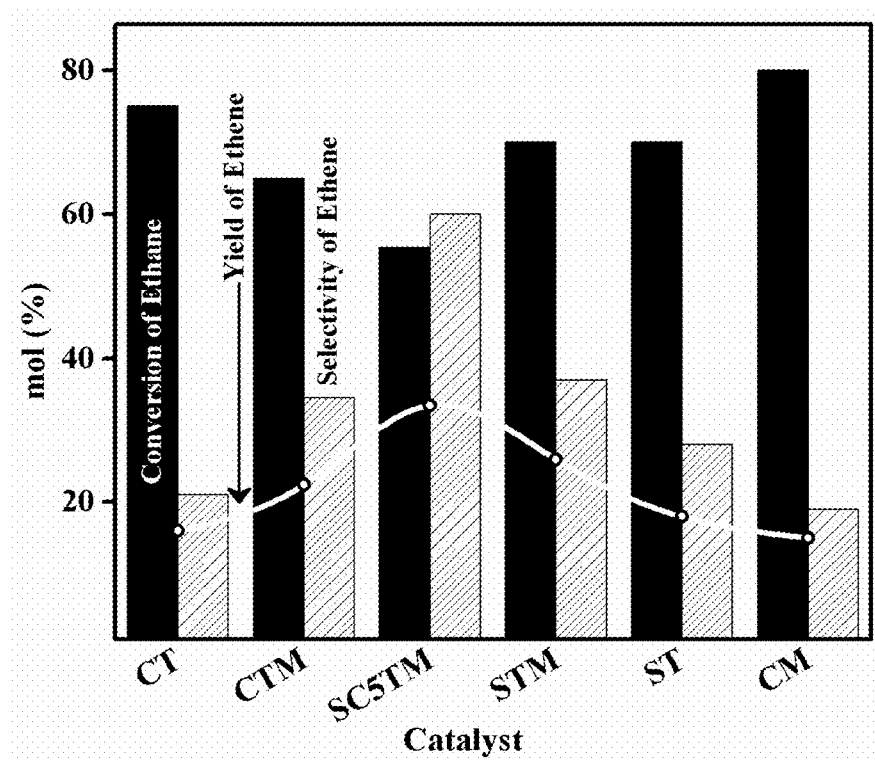
FIG. 4: depicts ODHE activity comparison for CT, ST and manganese substituted catalysts.

To study the effect of manganese in CT and ST matrix ODHE is done with catalysts CT, ST, CTM and STM at 650° C. with 6000 h$^{-1}$ reactant flow as shown in FIG. 4. It is observed that after manganese substitution in B-site the selectivity increased by 10%. Among these catalysts STM is more selective with 37% selectivity towards ethene. In this STM catalyst different ratio of calcium is substituted to understand the synergism between Ca and Sr. The activity and selectivity towards ethene increased as the amount of calcium increased reaching a maximum at Ca/Sr=1 and there is a decline in selectivity of ethene. This shows an optimum amount of Ca/Sr is required for a better activity. To optimize the amount of manganese in SC5TM different ratios of manganese substituted catalysts were prepared (0.075, 0.1 and 0.25). Among which the SC5TM gave a maximum selectivity and yield of ethene. SC5TM-25 give a comparable yield as SC5TM but eventually it decreased due to coke deposition as the increase in manganese content leads to over oxidation of ethane.

The wide angle PXRD patterns of freshly prepared catalysts are shown in FIG. 6. The diffraction peaks of crystalline Anatase phase are observed for the as synthesized catalysts. The crystalline nature of the materials remained intact even after the loading of cobalt. Raman spectra recorded for the synthesized catalysts were given in FIG. 7. The characteristic bands of Anatase are observed at 145 ($E_g$), 198 ($E_g$), 397 ($B_{1g}$), 514 ($A_{1g}+B_{1g}$) and 640 ($E_g$) cm$^{-1}$. Gradual decreases in the intensity of these peaks were observed with increasing cobalt loading. The absence of $Co_3O_4$ peaks even at maximum loading is the indication of incorporation of cobalt into the Titania lattice. The particles exhibited spherical morphology and the lattice fringes were identified as (101) planes of Anatase titania with interplanar distance of 0.345 nm as observed from TEM images. SAED pattern is also monitored and showed predominantly (101) plane of $TiO_2$. Presence of cobalt is evidenced from local EDX analysis.

The Oxidative dehydrogenation of n-butane (ODHB) is carried out in a fixed bed continuous flow mode reactor at atmospheric pressure in the temperature range 300-700° C. A catalyst volume of 1 mL sieved into a grain size ranging from 1.6 to 1.7 mm is placed in between two quartz wools in an inconel reactor tube. The major products are 1-butene, cis-2-butene, trans-2-butene, 1,3-butadiene, cracking products (ethane, ethene, propane, propylene) and combustion products ($CO_x$, water). The activity results are given in FIG. 8. Even the support itself is active for ODHB with 23% conversion and 15% selectivity for total butenes. With cobalt addition an observable increase in selectivity with a maximum 47% for 1.5CT indicates the role of cobalt. The conversion of n-butane had a parabolic trend with cobalt addition and 1.0CT giving maximum conversion of 33%. At higher cobalt loading, i.e., for 2.0CT there is a drastic decrease in selectivity due to the formation of more combustion products.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Preparation of Perovskite Catalysts, Characterization and Use

The metal precursors were dissolved in minimum amount of water along with citric acid (metal: citric acid in 1:3 ratio). For example in preparation of $CaTiO_3$, 25.2 g of citric acid is homogenized in 25 ml of water to which 4.72 g of calcium nitrate tetrahydrate and 5.68 g of Titanium isoproxide is added. After vigorous stirring the water is evaporated to get a gel which is kept in oven at 180° C. After drying a dry spongy material is obtained which is ground and calcined at 800° C. Series of Catalysts with different ratios of metal cations in A and B sites were prepared and denoted as given in Table 1 below.

TABLE 1

| Sr. No | Molar ratio | Code | Surface area (m$^2$/g) |
|---|---|---|---|
| 1 | $CaTiO_3$ | CT | 7 |
| 2 | $CaTi_{0.9}Mn_{0.1}O_3$ | CTM | 9 |
| 3 | $Sr_{0.3}Ca_{0.7}Ti_{0.9}Mn_{0.1}O_3$ | SC7TM | 12 |
| 4 | $Sr_{0.4}Ca_{0.6}Ti_{0.9}Mn_{0.1}O_3$ | SC6TM | 11 |
| 5 | $Sr_{0.5}Ca_{0.5}Ti_{0.9}Mn_{0.1}O_3$ | SC5TM | 8 |
| 6 | $Sr_{0.6}Ca_{0.4}Ti_{0.9}Mn_{0.1}O_3$ | SC4TM | 9 |
| 7 | $Sr_{0.7}Ca_{0.3}Ti_{0.9}Mn_{0.1}O_3$ | SC3TM | 10 |
| 8 | $Sr_{0.5}Ca_{0.5}Ti_{0.925}Mn_{0.075}O_3$ | SC5TM-075 | 11 |
| 9 | $Sr_{0.5}Ca_{0.5}Ti_{0.75}Mn_{0.25}O_3$ | SC5TM-25 | 7 |
| 10 | $SrTi_{0.9}Mn_{0.1}O_3$ | STM | 11 |
| 11 | $SrTiO_3$ | ST | 19 |
| 12 | $CaMnO_3$ | CM | 6 |

The catalytic activity for ODHE was tested using a fixed bed continuous flow reactor having two furnace zones over a temperature range of 350-700° C. at atmospheric pressure (atm.) with GHSV 6000 h$^{-1}$ flow of reactants ($O_2$/Ethane=1.5). In case of ODHB the temperature range was 400-500° C. with 1200 h$^{-1}$ flow of reactants ($O_2$/butane=1). The catalyst bed (1 cc) was loaded at the centre of the reactor with quartz wool packed in the spaces on either side of the bed which was filled with ceramic beads to fill the void. The catalyst was pelletized and sieved through the mesh size of 0.5-0.8 mm.

To study the effect of manganese in CT and ST matrix ODHE was done with catalysts CT, ST, CTM and STM at 650° C. with 6000 h$^{-1}$ reactant flow as shown in FIG. 4. It is observed that after manganese substitution in B-site the selectivity increased by 10%.

Among these catalysts, STM was more selective with 37% selectivity towards ethene. In this STM catalyst different ratio of calcium was substituted to understand the synergism between Ca and Sr. The activity and selectivity towards ethene increased as the amount of calcium increased reaching a maximum at Ca/Sr=1 and there was a decline in selectivity of ethene. This shows an optimum amount of Ca/Sr is required for a better activity. To optimize the amount of manganese in SC5TM different ratios of manganese substituted catalysts were prepared (0.075, 0.1 and 0.25). Among which the SC5TM gave a maximum selectivity and yield of ethene. The ODHE activity for different ratios of Ca/Sr and manganese is as shown in Table 2 below.

TABLE 2

ODHE activity for different ratios of Ca/Sr and manganese

| S. No | Catalyst | Conversion of $C_2H_6$ | Selectivity of $C_2H_4$ | Yield of $C_2H_4$ |
|---|---|---|---|---|
| 1 | SC3TM | 47.8 | 42 | 20 |
| 2 | SC4TM | 53.5 | 52 | 28.8 |
| 3 | SC5TM | 55.4 | 60 | 33.3 |
| 4 | SC6TM | 59.6 | 45 | 26.8 |
| 5 | SC7TM | 61.0 | 42.5 | 25.9 |
| 6 | SC5TM-25 | 66 | 50 | 33 |
| 7 | SC5TM-075 | 64 | 23.4 | 15 |

Reaction conditions: Total reactant flow ($C_2H_6$ & $O_2$) - GHSV 6000 h$^{-1}$, atm. pressure, 650° C., 1 cc catalyst.

To understand the effect of Temperature ODHE was carried out a wide range from 450-700° C. using SC5TM as the catalyst with 6000 h$^{-1}$ reactant flow. Below 450° C. there was no appreciable activity. It was observed that as the temperature increased the conversion of ethane and selectivity of ethene increased. The increase in selectivity of ethene is due to the decrease in electrophilic oxygen species found on the surface of the catalyst which causes total oxidation of ethane to $CO_2$. Above 650° C. cracking of ethane was maximum due to which cracked products like hydrogen and methane amount increased.

TABLE 3

ODHE activity over SC5TM at different temperatures

| S. No | Temperature (° C.) | Conversion of $C_2H_6$ | Selectivity (%) | | | |
|---|---|---|---|---|---|---|
| | | | $C_2H_4$ | $CO_2$ | $CH_4$ | $H_2$ |
| 1 | 450 | 32 | 36.9 | 52.5 | 0.3 | 7.5 |
| 2 | 500 | 34 | 40 | 50 | 0.2 | 7.4 |
| 3 | 550 | 37 | 43 | 46.5 | 0.5 | 7 |
| 4 | 600 | 42.3 | 48.9 | 41.6 | 1 | 6.9 |
| 5 | 650 | 55.4 | 61 | 28.8 | 1.8 | 8 |
| 6 | 700 | 92.6 | 23 | 19.8 | 14.7 | 42.6 |

Reaction conditions: Total reactant flow ($C_2H_6$ & $O_2$) - GHSV 6000 h$^{-1}$, atm. pressure, 1 cc catalyst.

To demonstrate the stability of the catalyst reaction was carried out for long time on stream conditions in optimized reaction conditions, i.e. 6000 h$^{-1}$, 650° C. and SC5TM as catalyst as shown in FIG. 5. After an initial decrease in conversion and increase in selectivity the activity remained stable for 24 hours. The minor decrease in activity was observed after 24 hours which was same as initial activity when the catalyst was regenerated with oxygen flow. SC5TM is also employed for ODHB at various temperatures and flow of reactants. Below 400° C. there was no appreciable activity for ODHB. At 400° C. and Butane/Oxy ratio 1 maximum yield of total butenes was obtained (11%). As the temperature was increased the conversion increased but the selectivity towards total butenes decreased. Based on this results 400° C. was considered to be the optimum temperature for the further studies. At 400° C. different ratios of butane/oxygen was altered to study the effect of reactant flow. When butane/oxygen ratio was 1 maximum yield (11%) was obtained which decreased when the flow ratios were altered as shown below in Table 4.

TABLE 4

ODHB at various temperatures

| S. No. | Temperature (° C.) | Butane/Oxy | Conversion of Butane (%) | Selectivity of total Butenes (%) | Yield of total Butenes (%) |
|---|---|---|---|---|---|
| 1 | 400 | 1 | 44 | 25 | 11 |
| 2 | | 0.5 | 73 | 6 | 4 |
| 3 | | 2 | 31 | 20 | 6 |
| 4 | 450 | 1 | 43 | 17 | 7 |
| 5 | 500 | 1 | 55 | 12 | 6.6 |
| 6 | 550 | 1 | 64 | 3 | 2 |

Example 2: Cobalt Incorporated Titania Catalyst Preparation, Characterization and Use Various cobalt incorporated titania catalysts were synthesized by glycine combustion method. All the chemicals were used as such purchased without any purification. Titanium isopropoxide, cobalt nitrate were used as Ti and Co precursors and glycine was used as fuel. In a typical synthesis procedure of xCT, different mol % of cobalt nitrate (x=0.5, 1.0, 1.5, 2.0 mmol) in 30 mmolTi precursor with glycine in 1:2 molar ratio of metal precursor to fuel after combustion at 100° C. on a hot plate were calcined at 450° C. Pure titania was also prepared for the comparison study. The wide angle PXRD patterns of freshly prepared catalysts were shown in FIG. 6. The diffraction peaks of crystalline Anatase phase were observed for the as synthesized catalysts. The crystalline nature of the materials remained intact even after the loading of cobalt. Raman spectra recorded for the synthesized catalysts were given in FIG. 7. The characteristic bands of Anatase are observed at 145 ($E_g$), 198 ($E_g$), 397 ($B_{1g}$), 514 ($A_{1g}+B_{1g}$) and 640 ($E_g$) cm$^{-1}$. Gradual decreases in the intensity of these peaks were observed with increasing cobalt loading. The absence of $Co_3O_4$ peaks even at maximum loading was the indication of incorporation of cobalt into the Titania lattice. The particles exhibited spherical morphology and the lattice fringes were identified as (101) planes of Anatase titania with interplanar distance of 0.345 nm as observed from TEM images. SAED pattern was also monitored and showed predominantly (101) plane of $TiO_2$. Presence of cobalt was evidenced from local EDX analysis.

The Oxidative dehydrogenation of n-butane (ODHB) was carried out in a fixed bed continuous flow mode reactor at atmospheric pressure in the temperature range 350-600° C. A catalyst volume of 1 mL sieved into a grain size ranging from 1.6 to 1.7 mm was placed in between two quartz wools in an inconel reactor tube. GHSV of total reactants was kept 1200 h$^{-1}$ with 1:1 ratio of n-butane to molecular oxygen and each run were made for 2-3 hrs. The effluent gases were analyzed using a Thermo Scientific Trace 1110 gas chromatograph coupled with both FID which is equipped with Alumina plot column and TCD equipped with Porapak Q and Molecular sieve columns. The major products were 1-butene, cis-2-butene, trans-2-butene, 1,3-butadiene, cracking products (ethane, ethene, propane, propylene) and combustion products ($CO_x$, water).

The effect of reaction temperature is investigated for a range of temperature from 350-600° C. over the optimized catalyst 1.0CT (Table 5). A steady increase in conversion was observed up to 500° C. with decrease in selectivity whereas the different behavior at 500° C. can be due to the particular composition of titania with a mixture of Anatase, Rutile and Brookite phases at that temperature. At 550° C., the maximum conversion was observed as 65% with negligible selectivity. This was owing to the formation of more cracking and combustion products. At highest studied temperature, i.e., 600° C., nearly complete cracking occurred. With molecular oxygen as oxidant, best results obtained at 400° C. and 10:10 ml/min n-butane to Oxygen flow with 33% conversion and 37% total butenes selectivity. Overall yield obtained is 12% with 56% 1-butene.

TABLE 5

ODHB on 1.0CT at different temperatures with 1:1 butane to oxygen flow with 1200 hr$^{-1}$ GHSV

| Sr. No. | Temperature (° C.) | Conversion of n-butane (mol %) | Selectivity of total butenes (mol %) | Yield of total butenes (mol %) |
|---|---|---|---|---|
| 1 | 350 | 24 | 39 | 9 |
| 2 | 400 | 33 | 37 | 12 |
| 3 | 450 | 35 | 26 | 9 |
| 4 | 500 | 32 | 15 | 5 |
| 5 | 550 | 65 | 1 | 0 |
| 6 | 600 | 100 | 0 | 0 |

Advantages of the Invention

One step process;
Production of butenes at a lower temperature;
Environmentally benign catalyst and economically cheap.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

We claim:

1. A process for conversion of alkanes to alkenes comprising contacting a feed stream comprising an alkane and an oxidant with a catalyst at a temperature of 350 to 700° C. to produce an alkene;
   wherein said catalyst is selected from an $ABO_3$ type perovskite $Sr_xCa_yTi_aMn_bO_3$ with "x" and "y" ranging from 0.1 to 0.9, "a" from 0.75 to 0.925 and "b" from 0.075 to 0.25, or is selected from the group consisting of $Sr_{0.3}Ca_{0.7}Ti_{0.9}Mn_{0.1}O_3$, $Sr_{0.4}Ca_{0.6}Ti_{0.9}Mn_{0.1}O_3$, $Sr_{0.5}Ca_{0.5}Ti_{0.9}Mn_{0.1}O_3$, $Sr_{0.6}Ca_{0.4}Ti_{0.9}Mn_{0.1}O_3$, $Sr_{0.7}Ca_{0.3}Ti_{0.9}Mn_{0.1}O_3$, $Sr_{0.5}Ca_{0.5}Ti_{0.925}Mn_{0.075}O_3$ and $Sr_{0.5}Ca_{0.5}Ti_{0.75}Mn_{0.25}O_3$.

2. The process as claimed in claim 1, wherein said alkane is selected from ethane or butane.

3. The process as claimed in claim 1, wherein said oxidant is selected from molecular oxygen ($O_2$) or carbon dioxide ($CO_2$).

4. The process as claimed in claim 1, wherein a ratio of alkane to oxidant is in the range of 1:1 to 1:5.

5. The process as claimed in claim 1, wherein said process is carried out in fixed bed reactors, fluidized bed reactors or continuous flow reactors.

6. The process as claimed in claim 1, wherein said process is carried out in a fixed bed continuous flow reactor.

7. The process as claimed in claim 1, wherein said process is carried out at atmospheric pressure.

8. The process as claimed in claim 1, wherein a yield of said alkene is in the range of 8 to 35 mol %.

* * * * *